US005344417A

United States Patent [19]

Wadsworth, Jr.

[11] Patent Number: 5,344,417

[45] Date of Patent: Sep. 6, 1994

[54] UNIVERSAL FITTING FOR INOCULATION RECEPTACLES

[75] Inventor: Gilbert A. Wadsworth, Jr., Cockeysville, Md.

[73] Assignee: Becton, Dickinson and Company, Franklin Lakes, N.J.

[21] Appl. No.: 943,625

[22] Filed: Sep. 11, 1992

[51] Int. Cl.[5] .............................................. A61B 19/00

[52] U.S. Cl. .................................... 604/414; 604/411; 604/403

[58] Field of Search ............... 604/403, 411, 412, 413, 604/414, 905; 141/383, 386

[56] References Cited

U.S. PATENT DOCUMENTS

| | | | |
|---|---|---|---|
| 2,689,562 | 9/1954 | Adams et al. | 604/412 |
| 2,893,389 | 7/1959 | Nesset | 604/412 |
| 4,505,709 | 3/1985 | Froning et al. . | |
| 4,564,054 | 1/1986 | Gustavsson | 141/383 X |
| 4,607,671 | 8/1986 | Aalto et al. | 604/415 X |
| 4,883,483 | 11/1989 | Lindmayer et al. | 604/411 |
| 4,927,605 | 5/1990 | Dorn et al. | 604/411 X |
| 5,067,950 | 11/1991 | Broadnax, Jr. | 604/411 X |

FOREIGN PATENT DOCUMENTS 89112256.6 1/1990 European Pat. Off. .

*Primary Examiner*—Robert A. Hafer
*Assistant Examiner*—Sam Rimell
*Attorney, Agent, or Firm*—Richard J. Rodrick

[57] ABSTRACT

A universal fitting for a receptacle into which an inoculum may be introduced or withdrawn for subsequent examination includes a body portion with a needle for introducing the inoculum into a receptacle or for withdrawing the inoculum from the receptacle. An annular skirt extends from the body portion for positioning over a liquid entry portion of the receptacle. The skirt has an internal surface and a plurality of ribs thereon projecting radially inwardly. These ribs are adapted to engage the entry portion of the receptacle for substantially centering the fitting on and securely gripping the fitting to the receptacle during introduction or withdrawal of the inoculum.

2 Claims, 4 Drawing Sheets

UNIVERSAL FITTING FOR INOCULATION RECEPTACLES

BACKGROUND OF THE INVENTION

1. Field of the Invention

The present invention relates to a universal fitting for a receptacle into which an inoculum may be introduced or withdrawn for subsequent examination, and more particularly, concerns such a fitting which is substantially centered on and securely gripped to such receptacle.

2. Background Information

When blood or other body fluids, taken from a patient, must be tested in the laboratory, it is common procedure to use specimen culture bottles or vials. These culture bottles are usually made of glass or plastic and include an entry portion sealed with a pierceable septum. This septum is usually made from rubber or other thermoplastic material which may be pierced by a sharp needle or cannula for introducing the liquid specimen into the bottle or for withdrawing a liquid specimen from the bottle. Once the needle is withdrawn, the rubber material of the septum reseals itself. It is also known to employ a septum with a small slit already included. Rather than use a sharp-pointed needle for penetration, this septum may be penetrated with a blunt cannula or like instrument.

While blood or other body fluids may be collected directly into any specimen culture bottle, it is typical to employ intermediate collecting devices to obtain the liquid samples. Blood samples from patients may be taken with a conventional syringe. This technique permits the technician to inoculate one or more blood culture bottles with the collected blood sample. In another technique, blood may be collected into an evacuated blood collection tube and sent to the lab. When the blood is ready for testing, the specimen may be withdrawn from the evacuated tube by use of a syringe and needle, and the blood is then inoculated into one or more blood culture bottles.

Whether blood is drawn directly or indirectly from the patient into a blood culture bottle or the like, it is desirable to use techniques which minimize the user's exposure to sharp-pointed needles. In this regard, it is known to use a fitting which is placed over the top of the culture bottle. The fitting may include a needle or cannula element so that when the fitting is placed over the entry portion of the bottle, the needle penetrates the septum and extends into the interior of the bottle. Then, a syringe with the blood or other body fluid may be connected to the fitting by a well-known luer connection, thus eliminating the use of a needle at the end of the syringe. Such fittings are described, for example, in U.S. Pat. No. 4,505,709 and European Patent Application 89112256.6.

Further improvements in the use of such a fitting have been sought. For example, improvements in maintaining the fitting securely in place on the culture bottle would be helpful. Further, and particularly where the septum in the culture bottle may have a previously fabricated slit, it would be helpful to be able to center the fitting as it is placed over the entry portion of the bottle. It is toward these and other improvements that the present invention is directed.

SUMMARY OF THE INVENTION

The present invention is a universal fitting for a receptacle, for the introduction or the withdrawal of an inoculum, comprising a body portion with means for receiving a needle through which the inoculum may pass into or out of the receptacle. An annular skirt extends from the body portion for positioning over a liquid entry portion of the receptacle. The skirt has an internal surface and a plurality of ribs thereon projecting radially inwardly. These ribs are adapted to engage the entry portion of the receptacle for substantially centering the fitting on and securely gripping the fitting to the receptacle during introduction or withdrawal of the inoculum.

In accordance with the principles of the present invention, a universal fitting is provided for blood culture bottles and the like. This fitting serves as a gripping device which centers and securely holds the outer surface of a culture bottle entry portion during introduction or withdrawal of the liquid sample. In the preferred embodiment of the invention, the bell-shaped skirt of the fitting enshrouds the needle which penetrates the culture bottle. Thus, this device minimizes the exposure of any sharp points in order to reduce the possibilities of being stuck with contaminated needles. Other advantages of the present invention may be learned from reading the Detailed Description which follows.

DETAILED DESCRIPTION

Figure 1:
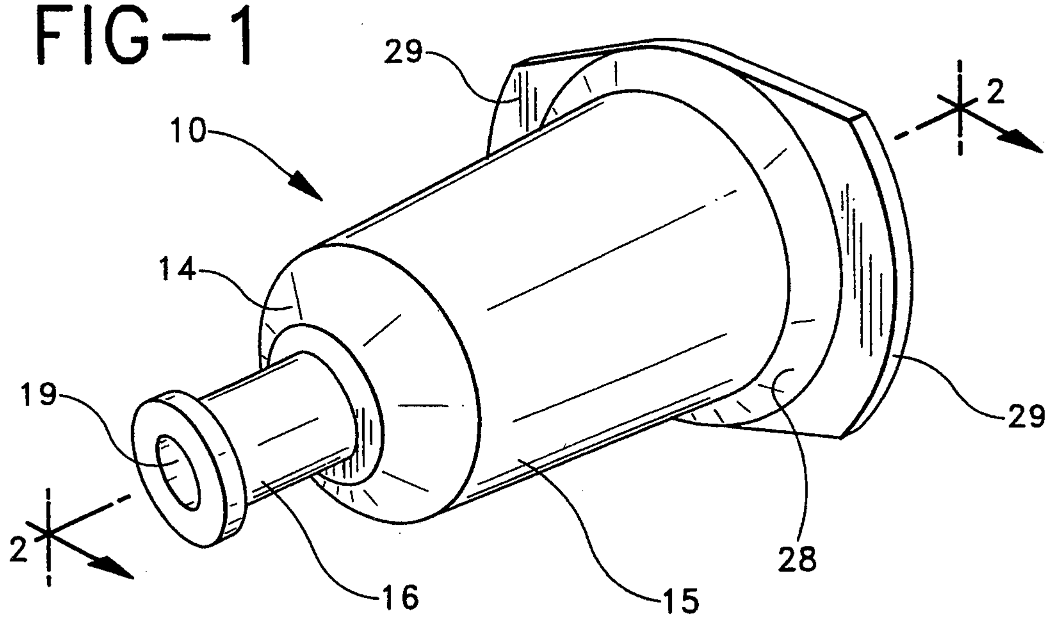
FIG. 1 is a perspective view of a preferred embodiment of the universal fitting of the present invention.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Figure 2:
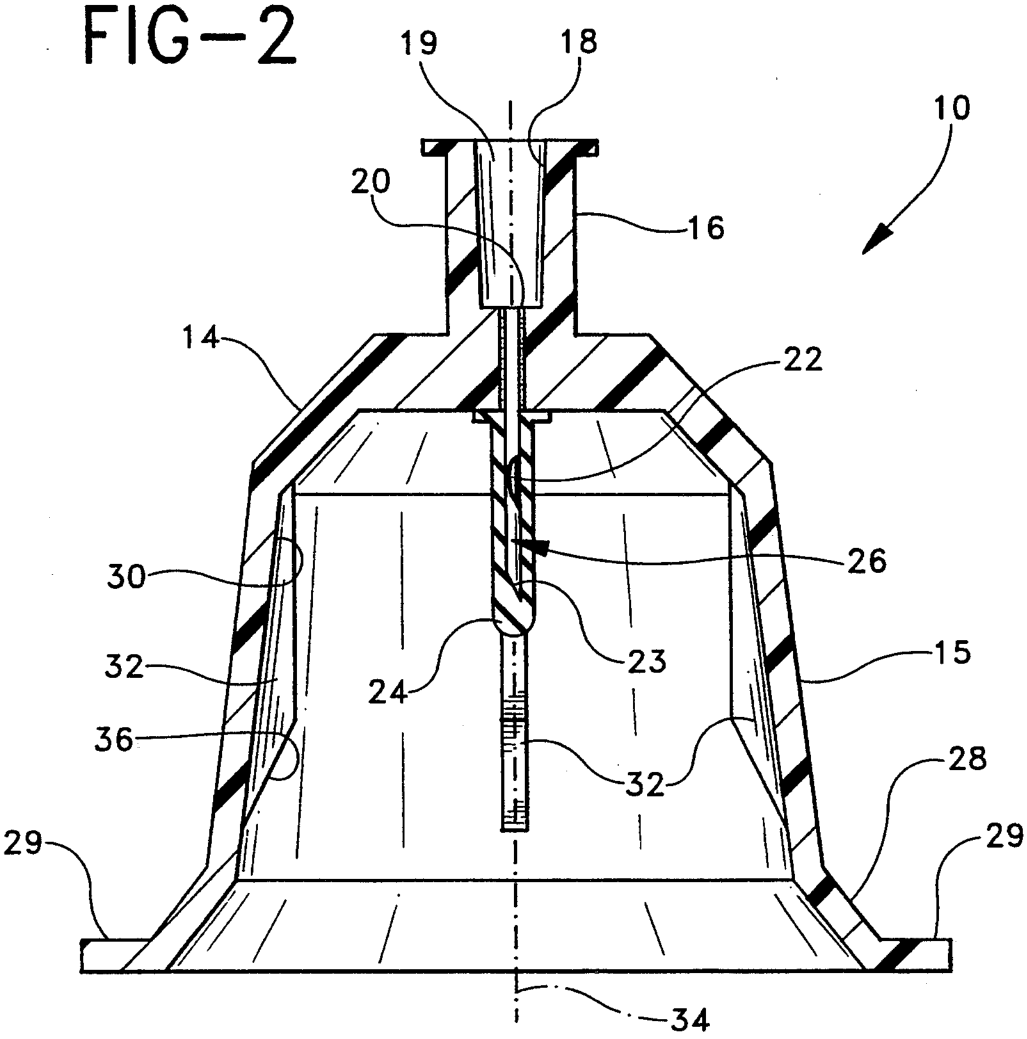
FIG. 2 is a cross-sectional view of the fitting of FIG. 1 taken along line 2—2 thereof.

Referring now to the drawings, and FIGS. 1 and 2 in particular, there is illustrated the preferred universal fitting 10 of the present invention. Universal fitting 10 has a body portion 14 and an annular skirt structure 15 extending from the body portion for positioning over a liquid entry portion of a culture bottle, as will be explained below.

In the embodiment of FIGS. 1 and 2, body portion 14 preferably has formed integrally therewith a female luer lock fitting 16 with an internal annular surface 18 defining a recess 19 for receiving a male luer lock fitting of a syringe or like device. Positioned and affixed or cemented by an adhesive centrally of body portion 14 is a needle 26. This needle has a lumen 22 extending therethrough terminating in an opening 20 which is in fluid communication with recess 19 of luer lock structure 16. Needle 26 terminates at its other end in a sharp point 23. An elastomeric sheath valve 24 preferably is attached to the bottom surface of body portion 14 and surrounds needle 26, including its point 23. This sheath valve is penetrable by the point of the needle as the needle is introduced into a culture bottle in conventional fashion. Also, upon withdrawal of the needle from the culture bottle, sheath valve 24 reseals itself for regulating the flow of liquid through the needle, as will be described in greater detail below.

With regard to the needle in the body portion of the universal fitting, the embodiment being described in which the needle has a sharp point is only one form of this particular element of the invention. It is within the purview of the present invention that the needle be in the form of a blunt-ended, hollow cannula. If the needle has a blunt end, it is typically used in circumstances where the culture bottle may have a prefabricated slit in its entry end or other opening compatible with the introduction of a blunt-ended implement. When the needle has such a blunt end, sheath valve 24 may or may not be included. Should the sheath valve be included with a blunt-ended cannula, the end of the sheath may be formed with a slit to facilitate penetration of the blunt cannula through the end of the sheath.

Other configurations of the needle arrangement in the body portion of the fitting are also contemplated in the present invention. For example, the needle may be removably connected to the body portion of the fitting, with screw threads or the like. Further, the needle may be integrally formed as part of the body portion of the fitting. These and other arrangements have been described in the published European patent application recited above, and will be addressed in conjunction with the description of FIG. 5, below.

Skirt 15 extends away from body portion 14 with a slightly outwardly tapered flair, so that the skirt is preferably a bell-shaped shroud. Also, it can be seen in the drawings that skirt 15 extends away from the body portion a greater distance than the extension of needle 26, so that the skirt completely enshrouds the needle. This arrangement provides additional protection against inadvertent needle sticks. Near the open end of skirt 15, is an outwardly-flaired shoulder 28 which merges into one or more flanges 29.

It is preferred that fitting 10 be fabricated as a single, integrally formed structural piece, out of the same material. It is further preferred that the material be plastic and that skirt 15 be relatively flexible so that it may be flexed under the influence of finger pressure particularly for removing the fitting from the culture bottle after use, as will be described in greater detail below.

Figure 3:
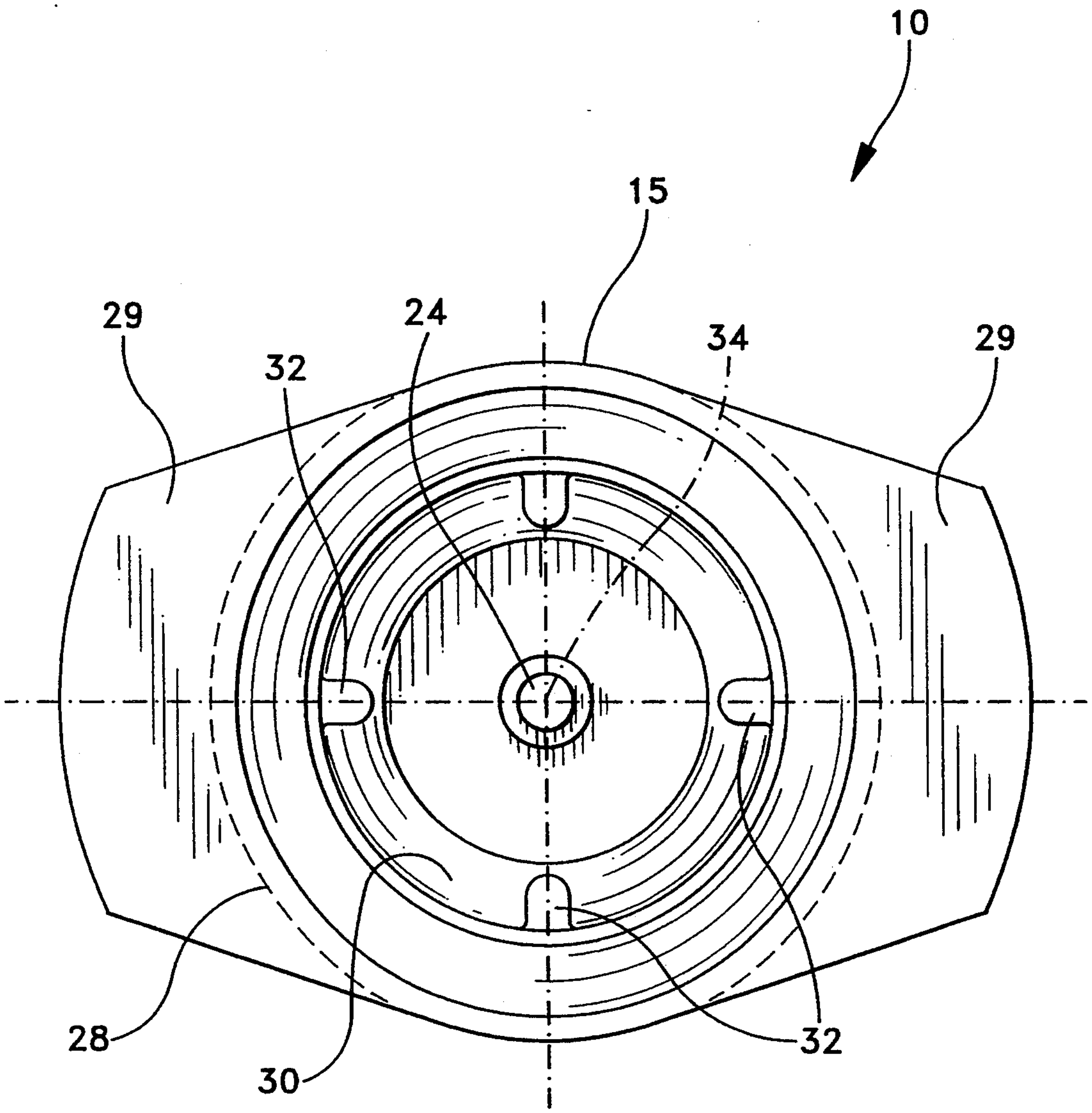
FIG. 3 is a reduced end view of the fitting of FIG. 1 as viewed from the open skirt end thereof.

As seen more particularly in FIGS. 2 and 3, skirt 15 includes an internal annular surface 30. Projecting radially inwardly from internal surface 30 are two or more ribs 32. In the embodiment being described, there are four such ribs substantially equally spaced from each other on internal surface 30. Equal spacing of the ribs around the internal surface is not a necessity. There could be an asymmetric pattern of the ribs on the internal surface which may help in the releasing of the grip between the fitting and the receptacle. However, the number of such projecting ribs may vary, but it is preferred that there be at least two ribs so that, in addition to providing a mechanism for gripping the culture bottle, the ribs also assist in centering the fitting onto the culture bottle.

Ribs 32 are arranged on internal surface 30 so that they run substantially parallel to a longitudinal axis 34 extending through the fitting. As ribs 32 extend along the internal surface toward the open end 35 of skirt 15, it is preferred that the ribs include a tapered segment 36. These tapers assist in centering the fitting over the culture bottle as the fitting is being placed thereon, and provide a gradually increasing interference fit between the fitting and the receptacle.

Figure 4:
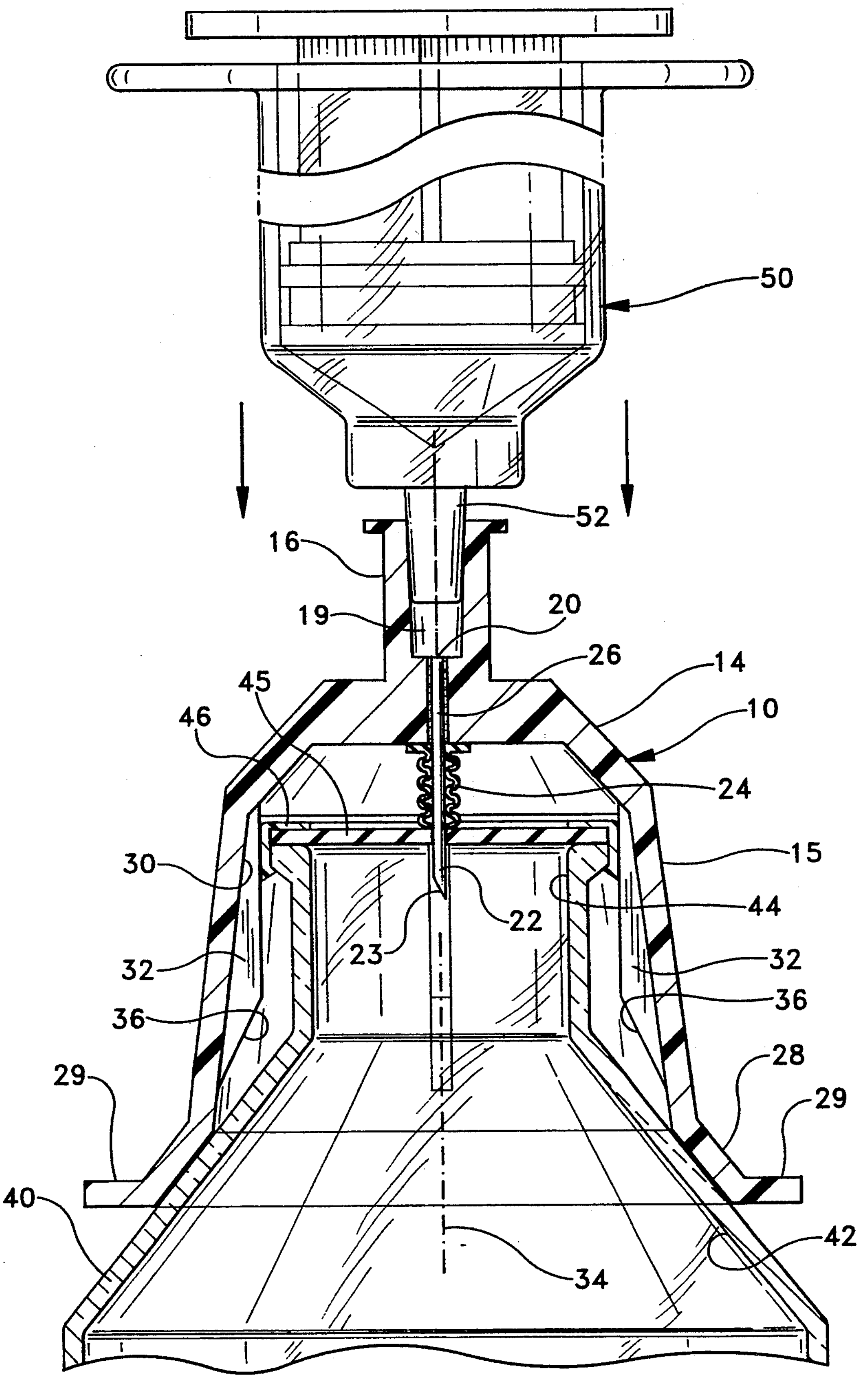
FIG. 4 is a cross-sectional view of the fitting of FIG. 1 as it may appear during use on a culture bottle with a syringe attached for the introduction or withdrawal of the liquid sample.

Operation of the fitting is illustrated in FIG. 4. A culture bottle 40 for culturing blood, body fluids or other inocula, typically has a neck portion 42 and an entry portion 44. This entry portion is generally an opening at the top of the bottle and includes a penetrable septum 45, which is preferably a self-sealing elastomeric membrane. A cap 46 holds the septum onto the opening of the culture bottle.

Fitting 10 is lowered over bottle 40 and is pushed down onto the entry portion thereof. Ribs 32 engage the annular surface of cap 44 around the opening of the bottle, thereby aligning fitting 10 to assure central penetration of the septum by the needle. As the fitting is pushed onto the bottle, needle point 23 first penetrates through sheath 24 and then penetrates through septum 45. It can be seen that sheath 24 folds, accordian-like, as it is compressed between body portion 14 of the fitting and septum 45 on the culture bottle. Also, shoulder 28 of the fitting is very closely aligned to neck portion 42 of the bottle. This close fit provides some degree of protection to the user in case the culture bottle is under positive pressure.

Once fitting 10 is pressed all the way down onto the entry portion of the bottle, the ribs securely grip the cap of the bottle for maintaining the fitting in position. At this time, liquid may be inoculated into the culture bottle or liquid contents withdrawn, as appropriate. To this end, a syringe 50 may be used to introduce an inoculum to or withdraw an inoculum from culture bottle 40. In this particular embodiment, syringe 50 typically includes a male luer connection 52 engaged with luer lock connection 16 on fitting 10.

After liquid has been introduced into or withdrawn from the culture bottle, fitting 10 may be disengaged from the bottle preferably by squeezing skirt 15 in the peripheral areas between the location of ribs 32. In this regard, the grip of ribs 32 against cap 46 is eased so that fitting 10 may be readily removed from the culture bottle.

Figure 5:
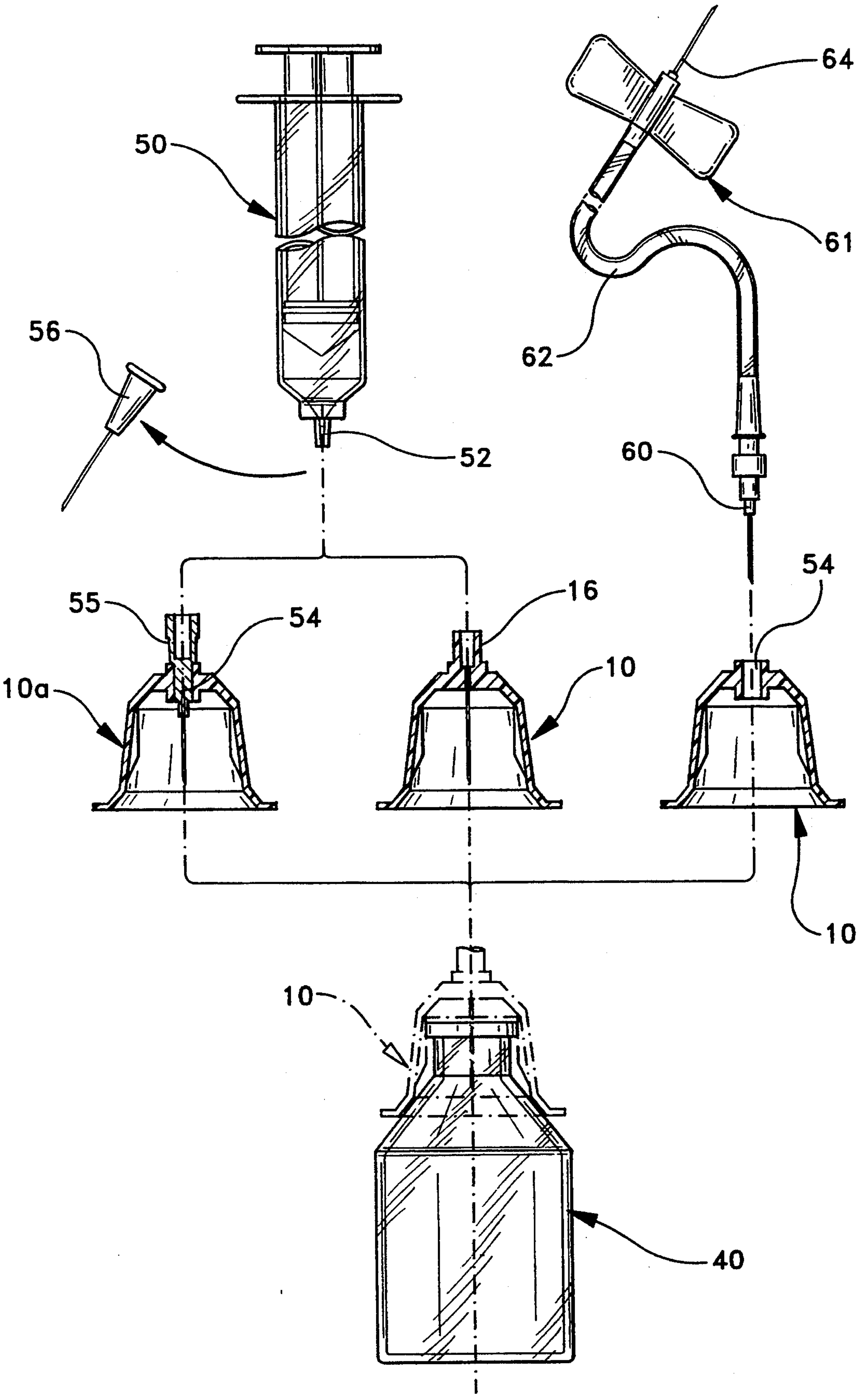
FIG. 5 is a schematic illustration of alternative uses of the fitting of the present invention.

It is appreciated that other liquid handling arrangements, instead of or in addition to a syringe, may be employed with the present invention. FIG. 5 illustrates some variations of the use of the present invention. For example, if syringe 50 is used to collect or deliver liquids, luer connection 52 may be introduced into mating fitting 16 of fitting 10 (illustrated as the middle embodiment of FIG. 5). This is the embodiment previously described in FIG. 4.

On the other hand, fitting **10*a* may include threads 54 in its body portion to receive a cannula 55. This cannula is attachable to syringe 52 by virtue of luer connection 52. Cannula 55 may be removed from fitting 10*a*** after use and discarded.

In another embodiment, fitting **10*b* is similar to fitting 10*a* in that threads 54 are provided. These threads also receive a cannula 60 as part of a tube set 61. This tube set includes a section of tubing 62 between cannula 60, which is connected to fitting 10*b*, and a second cannula or needle 64. Needle 64 may be used directly on a patient to draw blood through the tube set and into culture bottle 40, or may be used in evacuated collection devices to draw liquid out of culture bottle 40**, if so desired. Other variations of the use of the fitting described herein may come within the purview of the present invention.

Thus, the present invention provides a universal fitting for use with culture bottles, vials or the like which is securely held onto the bottle during introduction or withdrawal of liquids from the bottle and which enshrouds any sharp-pointed needle to thereby reduce the chances of inadvertent needle sticking.

What is claimed is:

1. A universal fitting assembly for a receptacle for the introduction or the withdrawal of an inoculum comprising:

a body portion;

a needle extending from said body portion for passing an inoculum into or out of a receptacle;

an annular skirt extending from said body portion and surrounding said needle for positioning over a liquid entry portion of said receptacle, said skirt having an internal surface and a plurality of ribs thereon projecting radially inwardly, said ribs adapted to engage the entry portion of said receptacle for substantially centering the fitting on and securely gripping the fitting to said receptacle during introduction or withdrawal of the inoculum; and a syringe connected to said needle.

2. A universal fitting assembly for a receptacle for the introduction or the withdrawal of an inoculum comprising:

a body portion;

a needle extending from said body portion for passing an inoculum into or out of a receptacle;

an annular skid extending from said body portion and surrounding said needle for positioning over a liquid entry portion of said receptacle, said skirt having an internal surface and a plurality of ribs thereon projecting radially inwardly, said ribs adapted to engage the entry portion of said receptacle for substantially centering the fitting on and securely gripping the fitting to said receptacle during introduction or withdrawal of the inoculum; and a tube set connected to said needle, said set including a second needle and a section of tubing interconnecting said needle and said second needle.

* * * * *